United States Patent
Roos et al.

(10) Patent No.: US 9,657,339 B2
(45) Date of Patent: May 23, 2017

(54) METHOD FOR AMPLIFICATION OF TARGET NUCLEIC ACID

(75) Inventors: Fredrik Roos, Loveland, CO (US); Henrik Johansson, Loveland, CO (US); Magnus Isaksson, Loveland, CO (US); Mats Nilsson, Loveland, CO (US); Olle (Olof) Ericsson, Uppsala (SE); Simon Fredriksson, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 872 days.

(21) Appl. No.: 13/512,924

(22) PCT Filed: Dec. 3, 2010

(86) PCT No.: PCT/EP2010/068837
§ 371 (c)(1),
(2), (4) Date: Aug. 3, 2012

(87) PCT Pub. No.: WO2011/067378
PCT Pub. Date: Jun. 9, 2011

(65) Prior Publication Data
US 2012/0289426 A1    Nov. 15, 2012

(30) Foreign Application Priority Data

Dec. 3, 2009  (GB) .................................. 0921264.8

(51) Int. Cl.
*C12Q 1/68* (2006.01)
(52) U.S. Cl.
CPC .................................. *C12Q 1/6837* (2013.01)
(58) Field of Classification Search
None
See application file for complete search history.

(56) References Cited

U.S. PATENT DOCUMENTS

2008/0194413 A1 * 8/2008 Albert .............................. 506/1

FOREIGN PATENT DOCUMENTS

| EP | 1 262 563 A2 | 12/2002 |
|----|----|----|
| WO | 99/49079 A1 | 9/1999 |
| WO | 03/083137 A2 | 10/2003 |
| WO | 03/104406 A2 | 12/2003 |
| WO | WO03104406 | 12/2003 |
| WO | 2005/111236 A1 * | 11/2005 |
| WO | WO2005111236 | 11/2005 |
| WO | 2010/066884 A1 | 6/2010 |

OTHER PUBLICATIONS

International Search Report from PCT/EP2010/068837 dated Feb. 17, 2011 (3 pages).
Second Office Action for China Patent Application No. 201080055136.2, mailed on Apr. 18, 2014, 3 pages.

* cited by examiner

*Primary Examiner* — Karen S Weiler (57) ABSTRACT

A method for amplifying a target nucleic acid is disclosed, which includes: (a) fragmenting a nucleic acid sample to create a target fragment comprising a target nucleic acid and two probe-complementary portions; (b) contacting said fragmented nucleic acid sample with a probe comprising two target fragment-complementary portions complementary to the probe-complementary portions of the target fragment; (c) rendering the fragmented nucleic acid sample single-stranded; (d) allowing the probe-complementary portions to hybridise with the target-fragment complementary portions; (e) if the probe in step (b) is not immobilised, immobilising the probe-target fragment hybrid on a solid phase via immobilisation moiety; (f) separating non-immobilised nucleic acid fragments from the solid phase; (g) contacting the solid phase with a ligase to ligate ligatable 5' and 3' ends of the target fragment whereby the target fragment is circularized; and (h) amplifying said circularized target fragment.

19 Claims, 1 Drawing Sheet

METHOD FOR AMPLIFICATION OF TARGET NUCLEIC ACID

The present invention relates to an improved method for amplifying target nucleic acids present in a nucleic acid sample. In such a method the sample is fragmented and fragments containing the target nucleic acid ("target fragments") are hybridised to provided probes which contain target fragment-complementary sequences arranged such that the target fragment adopts a circular conformation on hybridisation. The probes are immobilised to a solid phase, facilitating a separation step to remove non-target nucleic acids prior to ligation-mediated circularisation of the target fragment in the probe-target fragment hybrid. The circularised target fragments are then amplified, and the amplification products may be subjected to subsequent analysis by, e.g., nucleic acid sequencing, microarray, qPCR, etc. The invention is particularly directed to an improvement in which the hybridisation and ligation steps are separated and performed in discrete steps, in separate solutions, allowing e.g. unhybridised fragments and nucleic acids to be separated and removed, prior to the ligation. The method of the invention is particularly suited to the targeted amplification of nucleic acids in multiplex.

It is generally desirable to be able selectively to amplify, in multiplex, numerous genomic regions of interest, for example in order to analyse candidate regions implicated in a physiological or pathological condition. Particularly, with the advent of next generation parallel sequencing technologies, there is a need for methods which allow the ready preparation of samples of large genomic regions of interest, in order to overcome the bottleneck which arises in genomic analysis from the unsuitability of the polymerase chain reaction (PCR) for high multiplex amplification. Cost-effective targeted re-sequencing which fully exploits the sequencing throughput of next generation sequencers requires a method capable of specifically amplifying in parallel large numbers of target genomic sequences.

It is known from WO 99/49079 that one PCR-independent method for amplifying a target nucleic acid from a nucleic acid sample is to fragment the sample to generate a target nucleic acid-containing fragment, and to circularise the fragment by hybridising the fragment to a linear oligonucleotide probe designed to contain adjacent sequences respectively complementary to 5' and 3' terminal sequences of the fragment. The probe may be immobilised. The fragment is subsequently circularised by ligation of the adjacently-hybridised termini and is then amplified by rolling circle amplification (RCA). However, a multiplex implementation of such a method is not disclosed in WO 99/49079.

WO 01/38580 discloses an immobilised "anchor primer" which can circularise a target nucleic acid for subsequent amplification by, for example, RCA.

A solution-phase (non-immobilised probe) method for multiplex amplification of target nucleic acids from a sample of nucleic acids is disclosed in WO 2005/111236. In this method partially double-stranded probes, having single-stranded ends flanking a double-stranded portion, are hybridised via their single-stranded ends in a target-specific manner to both ends of target fragments resulting from fragmentation of the nucleic acid sample. A ligation step results in the probe-target fragment hybrid becoming circularised. The double-stranded region of the probe, one strand of which forms part of the circularised probe-target fragment hybrid, contains a primer pair motif which is common to the plurality of different target-specific probes used in a multiplex assay. Hence, PCR amplification of multiple target fragments can be achieved simultaneously whilst avoiding amplification artefacts which can result from the use of multiple, different primer pairs.

It has now surprisingly been found, in the context of a method using single-stranded or partially double-stranded probes as described in WO 99/49079 or WO 2005/111236, respectively, that by performing a separation step between hybridisation of the target fragments to the probes and the subsequent ligation (circularisation) unexpectedly good results may be achieved. In the separation step, the probe-target fragment hybrids are separated from the sample, and in particular from unhybridised fragments or other nucleic acids. Such an effect would not have been predicted. It generally would not be expected that a significant difference in the results obtained by such a method would be achieved by separating the probe-target fragment hybrids before the ligation step (i.e. after hybridisation and before ligation) as opposed to separating after the ligation step. Indeed, if the position of a separation step within the sequence of steps of such a method would be expected to have a material effect, it would be that separating after the ligation step would be advantageous on account of the binding of the target fragments to the probe being stabilised by ligation. Particularly, if the probe is immobilised, this would lead to the immobilisation of the target fragment being stabilised, thereby enhancing its separation from non-specifically immobilised nucleic acids. In fact, it has surprisingly been found that the opposite is true; the results obtained when the hybridisation and ligation steps are separated by a separation step (i.e. separation before ligation) are significantly better than those obtained in the absence of a separation step or when such a step follows the ligation step.

Without wishing to be bound by theory, it is believed that non-target "background" nucleic acid fragments, if not removed by a separation step prior to ligation, become inter- or intramolecularly ligated into readily amplifiable linear concatemeric or circular molecules. Any such molecules which survive a post-ligation separation step cause high levels of background amplification during the amplification step. It is thought that by separating target (probe-hybridised) from non-target fragments before ligation, any non-target fragments remaining on the solid phase after the separation step have a low probability of ligating due to their low concentration, and/or steric hindrance due to their attachment to the solid phase. A lower level of ligation of such fragments into readily amplifiable species results in markedly reduced levels of background amplification.

Accordingly, the present invention provides a method for amplifying at least one target nucleic acid in a nucleic acid sample, comprising:

(a) fragmenting the nucleic acid sample to create at least one target fragment comprising said target nucleic acid and comprising two probe-complementary portions, wherein at least one of said two probe-complementary portions is located at an end of the target fragment;

(b) contacting said fragmented nucleic acid sample with at least one probe which is provided with an immobilisation moiety and optionally is immobilised on a solid phase by means of said moiety, and which comprises two target fragment-complementary portions which are complementary in sequence to the probe-complementary portions of the target fragment, wherein said portions of the probe may be adjacent, or separated by an intervening non-target fragment-complementary portion;

(c) rendering the fragmented nucleic acid sample single-stranded, wherein the step may occur before, contemporaneously with or after step (b);

(d) allowing the probe-complementary portions of the target fragment to hybridise with the target fragment-complementary portions of the probe;

(e) if the probe provided in step (b) is not immobilised, immobilising the probe-target fragment hybrid on a solid phase by means of said immobilisation moiety;

(f) separating non-immobilised nucleic acid fragments from the solid phase;

(g) contacting the solid phase with a ligase to ligate, directly or indirectly, ligatable 5' and 3' ends of the target fragment whereby the target fragment is circularised, wherein where one of said probe-complementary portions of the target fragment is not located at an end of the target fragment, the ligatable end, other than that at which a probe-complementary portion is located, is created by the action of a flap endonuclease or an exonuclease; and (h) amplifying said circularised target fragment.

The method of the invention as described above may be used to amplify a single (i.e. a single species of, which will normally be present in many copies) target nucleic acid ("simplex format"), or a plurality of (i.e. a plurality of species of) target nucleic acids ("multiplex format") in which case a plurality of probes will be used. However it is possible that a single probe may be used in the method to amplify more than one target nucleic acid, in the event that the fragmented nucleic acid sample contains fragments which are sufficiently similar in sequence so as to be possible to hybridise to the probe, and hence to amplify in a method using the same probe. It is clear from the above that "single" probe means single species of probe and does not imply any limitation on the actual number of probe molecules used.

The term "plurality" as used herein means two or more (or at least two), more particularly 3 or more (or at least 3), or 4, 5, 6, 8, 10, 15, 20, 30, 50, 70, 100, 500, 1000, 2000, 5000 or 10,000 or more. For example, 10, 100, 1000 or 10000 different probes may simultaneously be used to amplify, respectively, 10, 100, 1000 or 10000 different target nucleic acids. When performed in multiplex, one or more libraries of probes may be used that have been designed specifically to amplify the fragments of a particular nucleic acid sample (for example, human genomic DNA), or one or more subsets thereof, produced by digestion with a particular restriction enzyme or combination of restriction enzymes. Thus, probe libraries may be designed which are specific for desired target sequence(s).

In a preferred embodiment, a plurality of target nucleic acids are amplified. Also preferred is the use of one or more libraries of probes to amplify one or more subsets of fragments of a particular nucleic acid sample, for example subsets of fragments thought to be associated with particular pathophysiological conditions.

The term "amplifying" is used broadly herein to include any means of increasing the number of molecules of a given nucleic acid sequence (e.g. of copying, or replicating a nucleic acid sequence), and includes exponential amplification mechanisms such as the well known PCR and its known variants and multiple strand displacement (MDA), as well as non-exponential mechanisms such as RCA (exponential variants of RCA also exist). Like RCA, and unlike PCR, MDA is an isothermal reaction which does not require temperature cycling (when a circular template is used, as is the case according to the method of the invention, MDA is synonymous with "hyperbranched RCA"; Lizardi P. M. et al, Nat Genet., 19(3), 225-32, 1998). In particular, the amplification method may involve extension (i.e. nucleotide chain extension) from a primer (i.e. primer-based amplification), and as noted above this may be a linear or an exponential amplification.

Such amplification methods may employ sequence-specific primers, i.e. primers designed to hybridise to particular known sequences in the target fragment, or "random" primers may be used, such as hexamers, which, as is known in the art, are statistically likely to find complementary sequences with which to hybridise in any target fragments of a reasonable length. The use of random primers is particularly useful in the method of the invention.

In one embodiment of the method of invention it may be preferable to carry out a selective amplification step, by which is meant that only specific (species of) circularised target fragments are amplified, i.e. one or more (species of) circularised target fragments. Alternatively put, the circularised target fragments may be selectively amplified such that not all circularised target fragments produced by the method are amplified. Such selective or targeted amplification may be achieved by any means known in the art, e.g. by manipulating the amplification reagents and/or conditions such that only circularised target fragments that contain a particular target sequence will be amplified. Hence, the amplification could be limited to a single (species of) circularised target fragment or to a group of (species of) circularised target fragments that comprise one or more common sequences, e.g. by RCA, PCR etc. Similarly, several groups of (species of) circularised target fragments, each with a different amplification target sequence, may be selectively amplified. In one embodiment, a single primer (or primer pair in the case of PCR) may be used to amplify more than one (species of) circularised target fragment, e.g. each (species of) circularised target fragment contains a common sequence or similar sequence which would enable the primers to hybridise to said sequence and prime amplification.

By "target nucleic acid" as used herein is meant a region of a nucleic acid in the sample which it is desired to amplify. This will generally be a part (or a portion or segment) of a longer nucleic acid molecule which may be present in the sample. Thus, it may be a region or stretch of a longer nucleic acid present in the nucleic acid sample. The target nucleic acid may be of any length, but in order to be amplified by the method of the invention must comprise or be contained within a fragment (the "target fragment") produced by the step of fragmenting the nucleic acid sample. The sequence of the target nucleic acid may not be known, providing that at least some of the corresponding target fragment is of known sequence in order to facilitate the design of the probe, which must be able to hybridise to the two probe-complementary portions of the target fragment.

The "nucleic acid sample" referred to above may be any sample which contains any amount of nucleic acid, from any source or of any origin, from which it is desired to amplify a target nucleic acid known (or suspected) to be comprised therein. More particularly, the sample may be any sample that contains nucleic acid. The nucleic acid contained in the sample may be DNA and/or RNA. The sample may be complex, e.g. whole genomic DNA or a fraction thereof. In this regard it may, for example, be a direct product of a nucleic acid isolation procedure, or of a cell lysis procedure, or it may be further be fractionated or purified in some way, e.g. it may contain nucleic acids which have been partially or fully separated in some way, or treated in any way. The sample may be from any eukaryotic or prokaryotic or viral source, e.g. may be of microbial (for example bacterial or fungal), plant, or animal (e.g. vertebrate, mammalian or primate) origin. In a particular aspect, the sample may be of human origin e.g. human genomic DNA.

Thus, the target nucleic acid is preferably genomic DNA. It may represent total genomic DNA or it may be a sub-fraction thereof.

In a first step (a) of the method the nucleic acid sample known (or suspected) to contain the target nucleic acid is fragmented to produce fragments, amongst which will exist (if the target nucleic acid is present in the sample, and if the method of fragmentation is selected appropriately) at least one (i.e. at least one species of) fragment containing the target nucleic acid. The term "fragmenting" is used broadly herein to include any means by which the nucleic acid in the sample may be fragmented or cleaved (i.e. divided or "cut" into smaller pieces or fragments). Thus, fragmentation may be carried out enzymatically, e.g. using restriction or other endonucleases or nucleases such as DNase, and/or physically, e.g. by nebulisation or sonication or any shear-based methods. Such physical methods result in unpredictable, non-sequence-specific fragmentation, as do certain (non-restriction) endonucleases. Thus both random, and predetermined (or site-specific) fragmentation is encompassed, but the latter is preferred. Accordingly, fragmentation using an enzyme which cleaves at a known or defined site is preferred, in other words enzymes which cleave sequence-specifically or structure-specifically, or, put another way, which cleave to generate ends of known (defined) or predetermined sequence, for example restriction endonucleases and flap endonucleases. However, also encompassed by the reference to "fragmenting" in step (a) is fragmentation of a nucleic acid sample which inherently may occur as a result of the age of a sample, the conditions in which it is stored and any treatment of the sample (e.g. fixation, such as in formalin-fixed paraffin-embedded samples), and the degradation to which these factors contribute. Any suitable class of restriction endonuclease may be used, including type II and type IIs enzymes. Alternatively, the cleaving (fragmenting) may be achieved using a flap endonuclease (FEN), wherein an added nucleic acid or oligonucleotide is only partially hybridisable, due to being partially double-stranded, to a sequence in the nucleic acid sample resulting in a protruding non-hybridised region of the nucleic acid sample adjacent to a hybridised region. This secondary structure is the substrate for a so-called structure-specific "flap endonuclease" enzyme which cleaves the nucleic acid sample at the junction of the hybridised and non-hybridised regions (Lyamichev V et al, Science., 260(5109), 778-83, 1993). The use of a flap endonuclease may be advantageous in the absence of a (known) restriction enzyme recognition sequence near to the target nucleic acid within the nucleic acid sample, as it allows cleavage (fragmentation) to be targeted at any region of known sequence. Flexibility in positioning the site of cleavage is thereby afforded. When using a flap endonuclease, a preceding physical fragmentation step may be desirable.

In a preferred embodiment, the fragmenting is effected by one or more restriction endonucleases.

Fragmenting means may be used in combination, e.g. the use together of two or more endonucleases, more particularly two or more restriction endonucleases, or the use together of an enzymatic and a physical means. Furthermore, the nucleic acid sample may be differently fragmented in separate aliquots, which aliquots are then pooled and together subjected to the remaining steps of the method of the invention. In certain cases, it may be appropriate and sufficient to fragment using a single restriction endonuclease, but in other cases the use of additional restriction endonucleases may be preferred.

Hence, the fragmenting may be achieved by separating the nucleic acid sample into a plurality of aliquots and fragmenting the respective aliquots with different means or different combinations of means, such means being for example restriction enzymes. Any number of aliquots of the sample may be differently treated, e.g. 2 or more, or 3, 4, 5, 6, 7, 8, 9, 10, 11, 12, 13, 14, 15 or 20 or more etc. A representative range may include 5 to 20, 5 to 18, or 5 to 15, but any range between any of the above-noted integers may be used. The aliquots are then subjected to the remaining steps of the method and may be pooled at any point during the method, for example before step (b), before step (c), before step (d), before step (e), before step (f), before step (g) or before step (h) to give the (single) nucleic acid sample referred to in the above method. Reference in step (a) above to "at least one target fragment comprising said target nucleic acid" (i.e. at least one species of such a target fragment) therefore reflects that fact that, if the sample is fragmented in separate aliquots by more than one (combination of) means, more than one target fragment comprising the target nucleic acid will be created.

Hence, in a particular embodiment, fragmenting is achieved by subjecting aliquots of a nucleic acid sample to respectively different combinations of one or more restriction endonucleases, and pooling said aliquots of fragmented nucleic acid sample prior to step (b) above.

Known heterozygous polymorphisms in the sample nucleic acid may be exploited by fragmenting the sample using, if possible, endonucleases which recognise a sequence inactivated in at least one instance by such a polymorphism. By designing probes targeted to the fragments produced in the presence, and absence, of cleaving at the polymorphic endonuclease recognition site said haplotype-specific fragments may independently be amplified.

In addition to comprising the target nucleic acid, the target fragment comprises two "probe-complementary portions". These portions may independently be separate from, or overlap partially or completely with, the target nucleic acid sequence which it is desired to amplify. The probe-complementary portions consist of a nucleotide sequence complementary to the sequence of the corresponding target fragment-complementary portions of the probe, referred to in step (b) above as "target fragment-complementary portions which are complementary in sequence to the probe-complementary portions of the target fragment". By "complementary", as used herein, is meant possessing functional complementarity, i.e. a level of complementarity sufficient to mediate a productive hybridisation with the above-mentioned portions of the probe, which encompasses 100% complementarity and degrees of complementarity less than 100%. 100% complementarity between the probe-complementary portions and the corresponding parts of the probe is preferred. A productive hybridisation is a hybridisation in which the "binding" between the probe and the target fragment is sufficient, e.g. stable or strong enough, to allow the probe-target fragment hybrid to be separated from the sample. In particular, it may be a hybridisation which is capable of templating the direct or indirect ligation of the probe-complementary portions, including in a particular embodiment a preceding flap endonucleolytic, or exonucleolytic, digestion. Direct ligation means that the probe-complementary portions of the target fragment (which constitute or form the "ligatable ends") are ligated to each other. Indirect ligation means that the probe-complementary portions of the target fragment (in other words the "ligatable ends") are ligated, not directly to each other, but via the intermediacy of one or more intervening (oligo)nucleotides. Thus, in the latter case, the probe-complementary portions of the target fragment hybridise to the probe in such a way that they are not immediately adjacent on the probe, but that there is a gap of one or more nucleotides between them. Such a gap may be "filled" by one or more "gap" oligonucleotide(s), which are complementary to this non-target complementary portion of the probe. This is described further below. Alternatively, the gap may be filled by extending a probe-complementary portion which lies at the 3' end of the target fragment. In the indirect embodiment, ligation is templated via an intervening non-target fragment-complementary portion of the probe.

The probe-complementary portions of the target fragment may be of the same or different lengths, and may each be of any length providing that they are "complementary" to the corresponding parts of the probe according to the meaning given above. Thus the probe-complementary portions may be 5 nucleotides long or of any length above 5 nucleotides e.g., 6, 7, 8, 9, 10, 11, 12, 13, 14, 15, 16, 17, 18, 19, 20, 30, 40 or 50 or any integer between or up to or above these. 20 nucleotides is preferred. As "complementary", as used in connection with the probe-complementary portions, refers to said portions as a whole rather than to the individual nucleotides (such that, as discussed above, a probe-complementary portion may not necessarily by consist of 100% complementary nucleotides), these probe-complementary portion lengths should be considered to mean that, if a probe-complementary portion is not 100% complementary to the corresponding part of the probe, the furthest-apart target fragment-complementary nucleotides of said portion delineate a stretch of nucleotides of such a length. As discussed below, the attainment of an approximately uniform Tm for target fragment hybridisation across all of the probes in a multiplex embodiment may influence or dictate the precise lengths of each target fragment-complementary probe portion of the respective probes, and therefore also the lengths of the corresponding probe-complementary portions of the respective target fragments).

At least one of the two probe-complementary portions must be located at the 5' or 3' end of the target fragment. By "at an end" as used in step (a) above is meant that a certain number of terminal residues of the at least one target fragment end constitute the probe-complementary portion, i.e. there are no nucleotides between the probe-complementary portion and the fragment end which are not complementary to the corresponding target fragment-complementary portion of the probe which is complementary in sequence to that probe-complementary portion (i.e. which are not part of the probe-complementary portion). Although, as discussed above, complementarity between the probe-complementary portions and the corresponding parts of the probe may not be 100%, the terminal nucleotide of a probe-complementary portion situated at an end of the target fragment should be complementary to the corresponding nucleotide in the probe. Preferably, complementarity between the probe-complementary portions and the corresponding parts of the probe is 100%. If one of the probe-complementary portions is not located at an end of the target fragment, i.e. is internal to the fragment, ligation of this probe-complementary portion directly or indirectly to the other probe-complementary portion will first require the use of a flap endonuclease or an exonuclease to create a ligatable end which is hybridised to the probe, i.e. derived from the internal probe-complementary portion. This is discussed further below.

In a preferred embodiment, both probe-complementary portions are located at the ends of the target fragment.

Once the nucleic acid sample has been fragmented, the fragmented sample is contacted with at least one probe. As discussed above, except for the situation wherein a single probe may be able to amplify two or more target fragments (which are sufficiently similar in sequence so as to be possible to hybridise to, and amplify using, the same probe), the number of (species of) probes used will correspond to the number of (species of) target fragment which it is desired to amplify. The probe is provided with (e.g. attached or conjugated to, or contains) an immobilisation moiety, i.e. a means for attaching the probe to a solid phase, and may or may not already be attached via such means to a solid phase ("immobilised"). Thus, the immobilisation moiety is used selectively to attach the probe-target fragment hybrid, before or after its formation in step (d) above, to a solid phase or support, including for example a particle such as a bead. Numerous examples of elements which may function as immobilisation moieties are known in the art and include, e.g., an affinity binding partner, e.g. biotin or a hapten, capable of binding to its binding partner, i.e. a cognate binding partner, e.g. streptavidin or avidin, or an antibody, provided on the solid phase or support. Thus the immobilisation moiety may be any "ligand" capable of binding to a binding partner or "receptor" therefor, which binding partner or "receptor" may be provided on the solid phase. Alternatively it may be any functional group (e.g. a chemical group) capable of participating in a reaction with a corresponding, or reactive, group present on the solid phase, such that a bond (which may be covalent or non-covalent) is formed between the respective groups, binding the immobilisation moiety (and thereby the probe) to the solid phase. The interaction between the probe and the solid phase may be mediated by click chemistry (Kolb H. C. et al, Angew Chem Int Ed Engl., 40(11), 2004-2021, 2001).

Preferred is the use of a probe carrying biotin at the 5' or 3' end, which can interact with an avidin or streptavidin moiety on the solid phase. The probe may be biotinylated during synthesis or subsequently using TdT and biotinylated nucleotides (Igloi, G. L., Schiefermayr, E., BioTechniques, 15, 486-497, 1993). The use of an amine group to immobilise the probe is also preferred.

The solid phase may be any of the well known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc. The support may be made of glass, silica, latex or a polymeric material. Suitable are materials presenting a high surface area for binding of the analyte. Such supports may have an irregular surface and may be e.g. porous or particulate e.g. particles, fibres, webs, sinters or sieves. Particulate materials e.g. beads are useful due to their greater binding capacity, particularly polymeric beads. Conveniently, a particulate solid support used according to the invention will comprise spherical beads. The size of the beads is not critical, but they may e.g. be of the order of diameter of at least 1 and preferably at least 2 µm, and have a maximum diameter of preferably not more than 10, and e.g. not more than 6 µm. Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173. However, to aid manipulation and separation, magnetic beads are advantageous. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the analyte binding steps. Particularly advantageous solid phases include very small particles which can efficiently contact a high proportion of the immobilisable probes. Such particles may further be useful by retarding the movement of a particle-attached target fragment through a gel, allowing separation from free, non-particle-attached (non-target) fragments. Alternatively, also preferred is the use of a chromatographic matrix modified with groups that can be reacted covalently or non-covalently with groups on the probe.

In a particular embodiment, the solid phase carries one or more streptavidin moieties. In the same or another embodiment, the solid phase is magnetic beads.

In addition to carrying or containing an immobilisation moiety, the probe comprises two "target fragment-complementary portions" which are complementary in sequence to the probe-complementary portions of the target fragment and are otherwise referred to herein as the "corresponding parts of the probe". These portions of the probe may be of the same or different lengths and may be of any length sufficient to mediate a productive hybridisation, as defined above, with the probe-complementary portions of the target fragment. Thus, they may be 5 nucleotides long or of any length above 5 nucleotides e.g., 6, 7, 8, 9, 10, 11, 12, 13, 14, 15, 16, 17, 18, 19, 20, 30, 40 or 50 or any integer between or up to or above these. 20 nucleotides is preferred. As for the probe-complementary portions, since "complementary" refers to these portions of the probe as a whole rather than to the individual nucleotides, these lengths should be considered to mean that, if such a portion is not 100% complementary to the corresponding probe-complementary portion of the target fragment, the furthest-apart target fragment-complementary (i.e. probe-complementary portion-complementary) nucleotides of said portion delineate a stretch of nucleotides of such a length. In multiplex embodiments wherein more than one probe is used, the precise length of each target fragment-complementary portion of the respective probes may be chosen such that all of the probes share a substantially uniform melting temperature (Tm) for hybridisation to the corresponding target fragments.

The two portions of the probe complementary in sequence to the probe-complementary portions of the target fragment may be immediately adjacent to each other in the probe, or may be separated by an intervening "vector" portion the sequence of which is not complementary to the target fragment. In certain embodiments the gap between the ends of a target fragment hybridised to a probe, which gap corresponds to the vector portion of the probe, is filled by hybridisation of a complementary oligonucleotide (herein referred to as a "gap oligonucleotide") to the vector portion. In such embodiments, the vector portion may be of any length sufficient to allow a productive hybridisation with the "gap oligonucleotide", wherein by productive hybridisation in this context is meant a hybridisation capable of templating the indirect ligation of the probe-complementary portions of the target fragment (i.e. ligation of the ligatable ends of the target fragment to the respective ends of the gap oligonucleotide which is hybridised to the intervening portion of the probe). The vector portion may be of any sequence, providing the sequence does not cause hybridisation with the target fragment. The gap oligonucleotide, which is complementary to the vector portion, may contain one or more primer-binding sequences for amplification of the target fragment which, when circularised in step (g) (in embodiments employing a probe comprising such an intervening portion), incorporates the gap oligonucleotide (known in the context of the circularised target fragment as "vector sequence"). Additionally or alternatively, the gap oligonucleotide may contain one or more "barcode" sequences which are arbitrary sequences of nucleotides which may be used diagnostically to identify the sample origin of a circularised target fragment in a multiplex embodiment wherein multiple samples (for example, patient samples) are processed in parallel according to the method of the invention. For example, different fragmented samples could independently be circularised and ligated using differently-barcoded probes and corresponding gap oligonucleotides according to the method, and then pooled before amplification and downstream analysis.

It will be seen that in a related embodiment more than one gap oligonucleotide might be used, which gap oligonucleotides hybridise to the non-target complementary portion of the probe in such a way that they, and the ligatable ends of the probe, are ligated together in sequence during the ligation step. In other embodiments, the gap between the ends of a target fragment corresponding to the vector portion of the probe may be filled by polymerase-mediated extension of the ligatable 3' end of the target fragment. Suitable polymerases are known in the art. Once said 3' end has been extended up to the ligatable 5' end, the ends may be joined in a ligation reaction.

Thus, the intervening vector portion may, for example, be 1 nucleotide long or of any length above 1 nucleotide e.g., 1, 2, 3, 4, 5, 6, 7, 8, 9, 10, 11, 12, 13, 14, 15, 16, 17, 18, 19, 20, 30, 40, 50, 100, 150 or any integer between or up to or above these.

The probe, or probes in a multiplex embodiment, may be generated from a combinatorial synthesis or microarray synthesis (Zhou X. et al, Nucleic Acids Res., 32(18), 5409-5417, 2004); Gnirke A. et al, Nat Biotechnol., 27(2), 182-189, 2009). Such a strategy can be used to produce a small amount of a highly complex probe library.

Before the target fragment can hybridise with the probe, the fragmented nucleic acid sample must be rendered single-stranded. This may be achieved by any means known in the art, such as denaturation, e.g. by heat or pH, or through the use of chemicals. Heat denaturation is preferred. As indicated in step (c) above, the fragmented sample may be made single-stranded at any point before the hybridisation step (d), i.e. before, during or after the contacting of the fragmented sample with the probe. Preferably, the fragmented sample is made single-stranded after step (b) above.

Once the fragmented, single-stranded nucleic acid sample is in contact with the probe, the target fragment will hybridise to the probe via its probe-complementary portions. On hybridisation of both probe-complementary portions of the target fragment to the corresponding parts of the probe, the sequence separating the two probe-complementary portions will loop away from the probe such that the hybridised target fragment adopts a substantially circular conformation. The "looped-away" sequence is preferably the majority or all of the target fragment sequence not present in the probe-complementary portions. Only in an embodiment wherein one of the probe-complementary portions is not at an end of the target fragment will the hybridised target fragment contain non-probe-complementary portion sequence which is not part of the looped-away, circular configuration (such sequence will form a protruding end not hybridised to the probe). Suitable conditions for achieving hybridisation of nucleic acids are well known in the art.

In a preferred embodiment, the probe-complementary portions of the target fragment are allowed to hybridise with the complementary portions of the probe in the presence of formamide. In such an embodiment hybridisation takes place in a solution containing formamide, leading to improved results. In a particularly preferred embodiment, the hybridisation solution contains the following components: between 1% and 50% formamide; between 10 mM and 2M monovalent cations; and EDTA. For example, 20% formamide; 1M NaCl; and 5 mM EDTA may be used. It will be appreciated that to obtain a suitable hybridisation stringency these components should be combined in appropriate ratios within the respective stated ranges, said ratios being selected appropriately for the temperature of the hybridisation, which in turn is influenced by the lengths of the probe-complementary portions of the target fragments and the corresponding parts of the probes. For example, a suitable temperature for the above-specified hybridisation solution would be 46° C., assuming probe-complementary portions and corresponding target fragment-complementary portions of approximately 20 nucleotides. The hybridisation solution may be added to the reaction mixture at the same time as the probe.

When the fragmented sample and probe have been incubated for sufficient time and under sufficient conditions, as are known in the art, to allow hybridisation, the probe-target fragment-hybrid, if the probe was not provided immobilised on a solid phase in step (b) above, is immobilised to a solid phase by means of the probe's immobilisation moiety. As is known in the art, such immobilisation may simply be achieved by contacting the hybridisation mixture containing the probe-target fragment-hybrid with a solid phase capable of interacting with the immobilisation moiety of the probe.

The immobilisation of the probe-target fragment hybrid advantageously facilitates separation of the hybrid from the other components in the reaction mixture, such as the non-target fragment "background" nucleic acid. Such separation may be by any means known in the art which allows the liquid component of a reaction to be removed from one or more solid phase components. For example, if magnetic beads are used as the solid phase, the liquid component of the reaction mixture may be selectively aspirated by micropipette whilst the beads are retained in the reaction vessel by means of a magnetic force applied to the side of the vessel. An alternative, assuming the use of a suitable "particulate" solid phase, would be the use of a gel to size-selectively purify the "large" solid phase particles from the "small" liquid phase components of the reaction mixture. If the solid phase is a vessel, or a well, separation may simply be achieved by removing the reaction medium from the vessel or well.

As discussed above the separation step, facilitated by the prior immobilisation of the probe or probe-target fragment hybrid, prior to ligation of the circularised target fragment significantly and unexpectedly improves the results obtained by the method of the invention. It is speculated that this may result from the removal of background nucleic acids, before the ligation step, which would otherwise become ligated into highly amplifiable species, resulting in high levels of background amplification and thereby markedly lowering the quality of the results of the method.

The separation step provides a further advantage in the context of the method of the invention being used to prepare samples for sequencing, for example targeted re-sequencing, using next generation sequencing technologies. Such sequencing technologies sequence all of the nucleic acid molecules present in the reaction vessel. Hence, even background nucleic acids which are not prone to problematic amplification can contaminate the sequencing analysis. This problem is reduced or avoided by the separation step which removes all nucleic acids other than the immobilised probe-target fragment hybrids.

Furthermore, as discussed in more detail below, the use of an immobilisable probe and a solid phase, which facilitates the separation step, makes possible the removal of the probe from the amplification step. Thus, in certain embodiments the circularised target fragment is detached from the probe and this leads to advantageous results due to the ability to remove the probe from the amplification step and thereby avoid potential interference by the probe. This may allow higher probe concentrations to be used.

In one embodiment, the separation is enhanced by the use of one or more washes of the solid phase. Washes to remove non-immobilised reagents from a solid phase are routine in the art. In a preferred embodiment the washing is performed in the presence of formamide. In a particularly preferred embodiment the washing solution contains any combination of the following components: between 1% and 50% formamide; between 10 mM and 2M monovalent cations; and EDTA. The washing solution and washing conditions (e.g. temperature) may be the same as the hybridisation solution and conditions, described above. As noted above, temperature and solution components may be optimised together.

Advantageously, the method of the invention allows high stringency conditions to be used during the hybridisation and washing steps such that the probe-target fragment hybrids may be robustly separated from background nucleic acids which otherwise are non-specifically amplified resulting in undesirable levels of amplified background nucleic acids. The method takes advantage of the intramolecular stacking effect which stabilises the hybridisation of immediately adjacently hybridised nucleic acids by increasing the melting point of the hybrid, permitting the use of high stringency conditions to remove non-specifically hybridised nucleic acids. Thus, it is known that two oligonucleotides hybridised adjacently (i.e. separated by a nick, not a gap) stabilise each other's hybridisation relative to hybridised oligonucleotides separated by a gap. This is the "stacking effect". It is also known that, relative to two unconnected oligonucleotides, two regions of a single oligonucleotide which are otherwise comparable to said unconnected oligonucleotides will hybridise to a complementary nucleic acid with greater stability since the close proximity of the connected regions means that if one region becomes released from the complementary nucleic acid it will remain in close proximity thereto due to the maintained hybridisation of the other region. The local concentration of the two regions in relation to each other will thereby decrease the dissociation rate since if one region becomes un-hybridised it will be restricted from diffusing freely, and the probability of re-hybridisation is consequently high. This is the "intramolecular effect". In the case of a target fragment hybridising to a probe according to the method of the invention, both effects occur and potentiate each other (intramolecular stacking effect).

Once the immobilised probe-target fragment hybrids have been separated from the reaction mixture and optionally washed one or more times, the solid phase is contacted with a ligase. Ligases suitable for joining the ligatable ends of the target fragment are known in the art and include, e.g., Tth DNA ligase, Taq DNA ligase, *Thermococcus* sp. (strain 9° N) DNA ligase (9° N™ DNA ligase, New England Biolabs), Ampligase™ (Epicentre Biotechnologies) and T4 DNA ligase. The ligase directly or indirectly ligates the ligatable 5' and 3' ends of the target fragment, resulting in circularisation of the target fragment. By "directly or indirectly" in step (g) above is meant that the ends of the target fragment may be ligated to each other, or to the end (e.g. each end) of a gap oligonucleotide, or that the ligatable 5' end of the target fragment is ligated to the ligatable 3' which has been extended to fill the gap corresponding to the vector portion of the probe, as discussed above.

The reference to "ligatable" 5' and 3' ends is to be understood to mean the ends of the target fragment which are amenable to ligation (i.e. are hybridised to the probe). In some embodiments, i.e. wherein one of the two probe-complementary portions is internal to the target fragment, one of said ligatable ends will not correspond to either of the ends of the target fragment generated by fragmentation of the target nucleic acid sequence. In an embodiment wherein one of the probe-complementary portions is not at an end of (i.e. is internal to) the target fragment the fragment end lacking a probe-complementary portion (i.e. the end "terminal" relative to the internal probe-complementary portion) will "protrude". The protruding end may the 5' end or the 3' end of the target fragment. The structure formed by this protruding end and the opposite probe-complementary portion-containing end, hybridised to the probe adjacent to the where the protruding end protrudes from the site of hybridisation to the probe of the internal probe-complementary portion, is a substrate for a flap endonuclease. As discussed above, a flap endonuclease "resolves" this secondary structure by cleaving off the protruding end to leave a ligatable end hybridised to the probe. As an alternative to the use of a flap endonuclease, a 3' or 5' exonuclease (as appropriate) may be used to degrade the protruding end to generate such a ligatable end. Suitable exonucleases are known in the art and include e.g. exonuclease I, exonuclease T and RecJ$_f$. Thus, in one embodiment the ligation step is preceded by the use of a flap endonuclease, or an exonuclease.

In a preferred embodiment the ligation of the ligatable probe ends takes place in the absence of formamide. Hence, in such an embodiment, and wherein the hybridisation of the target fragment to the probe occurs in the presence of formamide, the separation step, and optional washing steps, between the hybridisation and ligation steps serves to remove formamide from the latter step. The separation of the hybridisation and ligation steps, facilitated by the use of a solid phase, in addition to significantly reducing background amplification by preventing ligation of non-target fragments additionally facilitates the use of formamide selectively in the hybridisation step (and optional washing steps) which improves the stringency of the hybridisation and thereby further reduces the possibility of non-specific hybridisation to the probe and subsequent ligation of background nucleic acids.

Ligation (direct or indirect) of the ligatable 5' and 3' ends of the target fragment causes the target fragment to become circularised. Reference to "circularised target fragment" is to be understood to encompass, inter alia, a target fragment which has been circularised by indirect ligation, i.e. each end of the target fragment has been ligated to the end of a gap oligonucleotide complementary to an intervening vector portion in the probe (as discussed above) such that the resulting circular molecule contains the target fragment and gap oligonucleotide sequence.

The circularised target fragment is then amplified. Amplification may be by any means known in the art to amplify nucleic acids and may be selective or random. As discussed above, amplification may particularly occur by primer-mediated amplification and more particularly by PCR, RCA or MDA. It may be desired to use more than one of these amplification techniques. For each of these techniques, random primers, for example hexamers, or sequence-specific primers (i.e. designed to hybridise with pre-determined, known sequences in the target fragment) may be used. As is well known in the art, PCR requires two primers in opposing orientation and for this reason PCR is preferably used with sequence-specific primers. As is also known, RCA is an isothermal amplification method which typically employs a single (sequence-specific) primer to effect continuous amplification of a circular template, resulting in a linear concatemeric amplification product comprising multiple copies of the complement of the template. In the method of the invention the primer may be an added oligonucleotide or may be the probe. Variations of RCA may also be used according to the method of the invention, such as hyper-branched RCA which employs a second primer complementary to the concatemeric amplification product and operates by a strand displacement mechanism to effect geometric amplification of the template.

In a preferred embodiment the circularised target fragment is amplified by MDA using random primers, preferably random hexamers. Relative to conventional RCA using a single, sequence-specific primer, such MDA results in exponential amplification. The use of random primers allows priming from multiple sites on the circular template, as well as priming from the amplification products thereby produced which is facilitated by the use of a polymerase with strand-displacement activity. Suitable polymerases are known in the art, and phi29 polymerase is particularly preferred for RCA and MDA. For PCR, suitable enzymes are well known and include Taq polymerase. PCR may particularly be used in the method of the invention in embodiments in which the parts of the probe complementary to the probe-complementary portions of the target fragment are separated by an intervening portion, resulting in a gap oligonucleotide (vector sequence) complementary thereto becoming incorporated into the circularised target fragment, as discussed above. In such an embodiment, the vector sequence may contain binding sites for sequence-specific PCR primers, to facilitate PCR amplification of the target fragment. The binding sites and corresponding primers may be arranged and designed such that the primers are outward-facing with respect to the vector sequence, resulting in amplification across the target fragment sequence. As discussed above, the vector sequence may additionally or alternatively contain barcode sequences. Barcoding of circularised target fragments to allow subsequent sample identification may also be achieved by using vector sequence containing binding sites for sequence-specific PCR primers, but no barcode sequences, together with PCR primers specific for such binding sites equipped with 5' tails which comprise barcode sequences. The barcode sequences are incorporated into the amplification product and are available to be "read" in a subsequent step such as nucleotide sequencing. This avoids the need to provide differently-barcoded probes and corresponding gap oligonucleotides for each sample to be identified. Different fragmented samples may therefore independently be circularised and ligated using the same probes and corresponding gap oligonucleotides according to the method, amplified using barcoded PCR primers, and the amplification products then pooled for downstream analysis.

In another embodiment, the vector sequence may contain binding sites for sequence-specific primers for use in sequence-specific primer MDA. In such a case, one primer would be provided which is specific for a binding site in the vector sequence and a second primer would be provided which is complementary to a sequence in the amplification product generated from the first primer (i.e. complementary to the target fragment) which corresponds to part of the vector sequence.

In a particular embodiment of the method of the invention, an initial amplification step by random primer MDA is followed by a PCR amplification step primed from the vector sequence. In a further embodiment, an MDA amplification step using random primers or primers specific for primer binding sites in the vector sequence of the circularised target fragments is followed by a PCR amplification step wherein the PCR primers, which are specific for primer binding sites in MDA product corresponding to the vector sequence, comprise barcode sequences in 5' tails.

It may be advantageous in certain embodiments, particularly where high concentrations of probe are to be used, to detach the circularised target fragment from the immobilised probe prior to the amplification step. This is to prevent an inhibition of amplification by polymerases such as phi29 which could occur in the presence of high concentrations of free 3' probe ends; such polymerases have 3' exonucleolytic activity resulting in association to free 3' ends at the possible expense of amplification of the circularised target fragment. High probe concentrations can potentially also impair PCR amplification-based embodiments as the probe is of complementary sequence to PCR primers which have binding sites in the vector sequence. This can inhibit annealing of the PCR primers with the circularised target fragment. This can be avoided by removing the circularised target fragment from the immobilised probe and separating the former from the solid phase. Such a separation step is routine in the art and is analogous to the earlier separation step, discussed above. The circularised target fragment may be detached from the immobilised probe by any means known in the art for un-hybridising hybridised nucleic acids. Preferably, the circularised target fragment is denatured from the probe. This may be achieved by any means known in the art, such as by heat or pH, or through the use of chemicals. Heat denaturation is preferred. Alternatively, the probe can be removed using an exonuclease or, if the probe consists in part of uridine residues, by the use of uracil-N-glycosylase (UNG). In addition to allowing the use of high concentrations of probe, the step of separating the probe from the circularised target fragment prior to amplification has the further advantage that probe-dependent non-specific amplification is eliminated.

The amplified target fragment, containing the target nucleic acid, may be used for any desired purpose, and many possible uses will be readily apparent to the skilled reader. As discussed above, the amplification of target nucleic acids by the method of the invention, particularly when performed in multiplex using a plurality of probes to amplify a plurality of target fragments, is particularly useful in sample preparation for parallel sequencing, such as targeted re-sequencing of multiple large genomic regions of interest, using next generation sequencing technologies. Such technologies include massive parallel sequencing platforms such as SOLiD (Applied Biosystems, Inc.), Illumina Genome Analyzer (Illumina, Inc.) and Genome Sequencer (454 Life Sciences).

The invention provides kits for use in the method of the invention. Such a kit will at least comprise one library of probes comprised of probes specific for all or a subset of the fragments produced by digestion of a nucleic acid sample (for example, human genomic DNA) with a particular restriction enzyme or combination(s) of restriction enzymes. The kit may contain more than one library of probes, i.e. multiple libraries respectively comprising probes specific for fragments produced by different restriction enzymes or combinations thereof and/or respectively comprising probes specific for different subsets of the fragments produced by digestion of a nucleic acid sample. As discussed above, the probes carry or contain an immobilisation moiety. In a preferred embodiment, said moiety is biotin (i.e. the probes are biotinylated).

The kit may further comprises one or more of the following components. Firstly, one or more restriction enzymes. If the kit comprises more than one restriction enzyme these may be provided individually or combined, or both (i.e. combinations and single enzymes may be provided). Preferably, the provided enzymes or combinations of enzymes correspond with the probe library or libraries comprised in the kit, such that the probes of a provided library are designed to amplify the fragments of a particular nucleic acid sample produced when said sample is digested with a restriction enzyme or combination of enzymes provided in the kit.

Secondly, a ligase may be provided in the kit, optionally together with the appropriate buffer. Suitable ligases for use in the method of the invention are known. For example, the kit may contain Tth DNA ligase, Taq DNA ligase, *Thermococcus* sp. (strain 9° N) DNA ligase (9° N™ DNA ligase, New England Biolabs), Ampligase™ (Epicentre Biotechnologies) or T4 DNA ligase. Tth DNA ligase is preferred.

Thirdly, the kit may comprise amplification reagents such as a polymerase, buffers and/or primers. The polymerase may be a polymerase known to be suitable for use in a PCR (e.g. Taq polymerase), or a polymerase known to be suitable for use in the amplification of a circular template (e.g. phi29 polymerase). Provided primers may be sequence-specific primers, optionally in pairs, or may be random primers such as random hexamers. The primers may contain 5' tails comprising barcode sequences.

Fourthly, a solid phase may be provided in the kit. Possible solid phases are as discussed above. The solid phase will be conjugatable to the immobilisation moiety on the probe. Preferably, the solid phase will carry a streptavidin moiety. Particularly, the solid phase is a streptavidinated microbead, such as a magnetic particle.

Fifthly, the kit may comprise a gap oligonucleotide complementary to an intervening portion, if present, between the parts of the probe complementary to the probe-complementary portions of the target fragment. The gap oligonucleotide may contain primer-binding sequences and/or barcode sequences. Alternatively or additionally, the kit may comprise a polymerase capable of extending the ligatable 3' end of the target fragment when hybridised to the probe, if said probe has such an intervening portion.

Further possible components of the kit which may be included in any combination with each other and with the components described above are: a flap endonuclease; an oligonucleotide to facilitate flap endonucleolytic cleavage of the nucleic acid sample; a 5' or 3' exonuclease; formamide; and UNG.

In addition to the above components, the kit may further include instructions for practicing the method of the invention. These instructions may be present in the kit in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a remote site. Any convenient means may be present in the kit.

Hence, in a further embodiment of the invention is provided a kit for amplifying a plurality of target nucleic acids in a nucleic acid sample, comprising one or more libraries of probes wherein said libraries are respectively comprised of probes specific for all or a subset of the fragments produced by digestion of a nucleic acid sample with a particular restriction enzyme or combination thereof and/or are respectively comprised of probes specific for different subsets of the fragments produced by digestion of a nucleic acid sample, and wherein said probes carry or contain an immobilisation moiety, in addition to one or more of the following components:

(i) one or more restriction enzymes, wherein said enzymes are provided individually and/or combined and wherein said enzymes and/or combinations thereof correspond with the enzymes and/or combinations thereof used to produce the fragments of said nucleic acid sample for which the probes of said one or more libraries are specific;

(ii) a ligase;

(iii) a polymerase and/or amplification primers optionally having 5' tails comprising barcode sequences;

(iv) a solid phase;

(v) a gap oligonucleotide optionally comprising primer binding sequences and/or barcode sequences;

(vi) a flap endonuclease;

(vii) a 5' or 3' exonuclease;

(viii) an oligonucleotide to facilitate flap endonucleolytic cleavage of the nucleic acid sample;

(ix) formamide; and (x) UNG.

The invention will be further described with reference to the following non-limiting Example with reference to the following drawing in which.

EXAMPLE

Restriction Digestion

Figure 1:
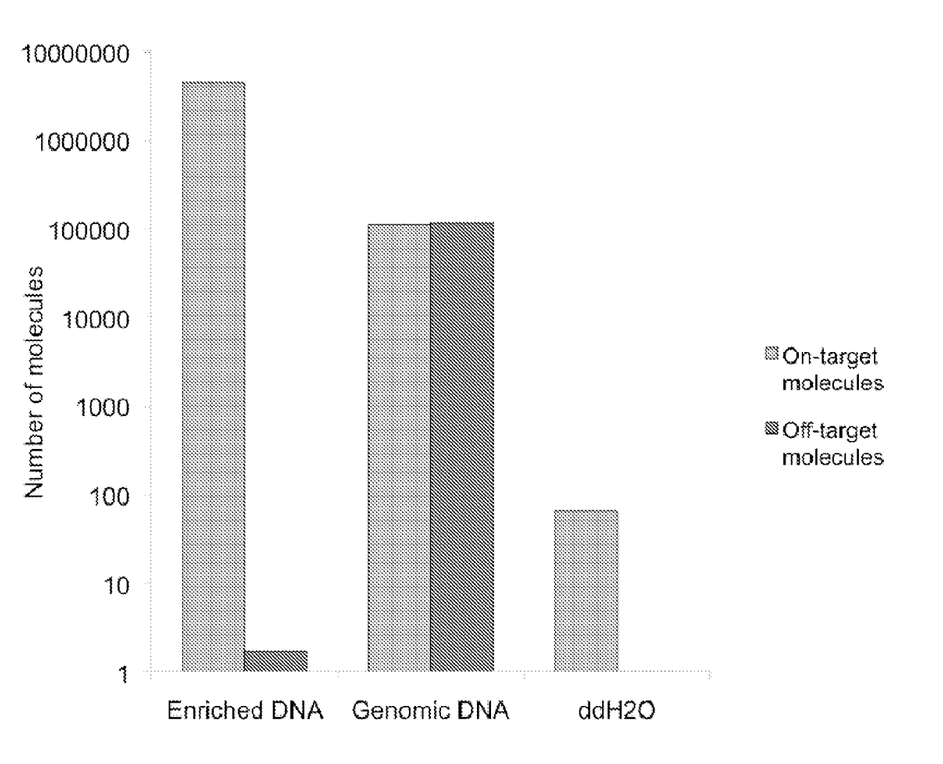
FIG. 1 shows the average number of molecules detected in the eight different PCR reactions from on-target and off-target regions. Virtually no off-target region fragments are left in the sample after enrichment.

Each sample was split up into eight different reactions constituting 100 ng DNA. All reactions contained 1 unit of each restriction enzyme, the corresponding reaction buffer and 85 ng BSA in a total volume of 10 µl . The eight reactions were SfcI and Hpy188I in NEB buffer 4; DdeI and AluI in NEB buffer 2; MseI and Bsu36I in NEB buffer 3; MslI and BfaI in NEB buffer 4; HpyCH4III and Bsp1286 in NEB buffer 4; SfcI and NlaIII in NEB buffer 4; MseI and HpyCH4III in NEB buffer 4; HpyCH4V and Eco01091 in NEB buffer 4. The reactions were incubated at 37° C. for 60 min and deactivated at 80° C. for 20 min before pooling.

Probe Hybridization

The 80 µl of pooled reactions were mixed with 1.6 µl 1 nM (individual concentration) biotinylated probes, 28 µl 4×Bind & Wash buffer (1× B&W buffer constitutes 1 M NaCl, 5 mM Tris-HCl (pH 8.0) and 5 mM EDTA) and 37 µl 100% formamide in a total volume of 160 µl. The solution was incubated at 95° C. for 10 min, 75° C. for 30 min, 68° C. for 30 min, 55° C. for 30 min and 46° C. for 10 hours.

Solid Phase Capture

The biotinylated probes were captured by adding 10 µl M-280 streptavidin coated magnetic beads, $6.7 \times 10^8$ beads/ml (Life Technologies), 10 µl 4× B&W buffer and 20 µl $H_2O$ to the reaction and incubating at room temperature for 10 min. After incubation the supernatant was discarded using a magnet. To remove non-specifically bound DNA the beads were washed with 200 µl 1× B&W buffer comprising 20% formamide at 46° C. for 30 min with rotation.

Circularization of Targeted Fragments

The beads were then incubated in 50 µl ligation mixture comprising: 12.5 U Ampligase (Epicentre), 1× reaction buffer (10× reaction buffer comprises 200 mM Tris-HCl (pH 8.3), 250 mM KCl, 100 mM $MgCl_2$, 5 mM NAD and 0.1% Triton® X-100; Epicentre) and 0.02 µg/ul BSA at 55° C. for 15 min.

Amplification

To enrich the circularized molecules the sample was amplified using Templiphi (GE Healthcare). Before amplification the ligated circles were denatured off the probes immobilized on the beads using 5 µl Templiphi sample buffer (GE Healthcare) at 95° C. for 10 min, and the supernatant was subsequently collected. The collected volume was then combined with a 5 µl volume comprising 4.5 µl reaction buffer and 0.5 µl enzyme mix and incubated at 30° C. for 4 hours, followed by heat deactivation at 65° C. for 10 min.

Enrichment Validation-qPCR Quantification of Target Regions

To validate the amplification of the targeted regions and evaluate the enrichment efficiency eight quantitative PCR (qPCR) reactions amplifying on-target (enriched) sequences were run alongside eight qPCR reactions amplifying off-target (not enriched) regions. For each of the 16 PCR reactions, 10 µl of a 1:200 dilution of the Templiphi amplification product was amplified in a 30 µl PCR mix comprising 2 mM $MgCl_2$, 1× PlatinumTaq buffer (20 mM Tris-HCl (pH 8.4), 50 mM KCl), 0.2 mM of each dNTP, 1× Sybr green and 167 nM of each primer. The reactions were cycled using the following protocol: 95° C. for 5 min, 40× (95° C. for 15 s, 56° C. for 30 s, 72° C. for 15 s) using a MX 3000 instrument (Stratagene). Cycle thresholds were determined using the accompanying software. The number of molecules was estimated assuming that a cycle threshold value of 40 corresponds to 1 molecule and that one PCR cycle doubles the number of amplicons. A gDNA sample comprising a known number of genomes was used to establish a reference point for quantification.

The invention claimed is:

1. A method for amplifying at least one target nucleic acid in a nucleic acid sample, comprising:

(a) fragmenting the nucleic acid sample to create at least one target fragment comprising said target nucleic acid and comprising two probe-complementary portions, wherein at least one of said two probe-complementary portions is located at an end of the target fragment;

(b) contacting said fragmented nucleic acid sample with at least one probe which is provided with an immobilization moiety and optionally is immobilized on a solid phase by means of said moiety, and which comprises two target fragment-complementary portions which are complementary in sequence to the probe-complementary portions of the target fragment, wherein said portions of the probe may be adjacent, or separated by an intervening non-target fragment-complementary portion;
(c) rendering the fragmented nucleic acid sample single-stranded, wherein the step may occur before, contemporaneously with or after step (b);
(d) allowing the probe-complementary portions of the target fragment to hybridize with the target-fragment complementary portions of the probe;
(e) if the probe provided in step (b) is not immobilized, immobilizing the probe-target fragment hybrid on a solid phase by means of said immobilization moiety;
(f) separating non-immobilized nucleic acid fragments from the solid phase;
(g) contacting the solid phase with a ligase to ligate, directly or indirectly, ligatable 5' and 3' ends of the target fragment whereby the target fragment is circularized, wherein where one of said probe-complementary portions of the target fragment is not located at an end of the target fragment, the ligatable end, other than that at which a probe-complementary portion is located, is created by the action of a flap endonuclease or an exonuclease; and
(h) amplifying said circularized target fragment.

2. The method of claim 1 for amplifying a plurality of target nucleic acids in a nucleic acid sample, wherein in step (b) the fragmented nucleic acid sample is contacted with a plurality of probes.

3. The method of claim 1, wherein in step (a) said fragmenting is by means of subjecting aliquots of said nucleic acid sample to respectively different combinations of one or more restriction endonucleases, and pooling said aliquots of fragmented nucleic acid sample prior to step (b).

4. The method of claim 1, wherein both probe-complementary portions are located at the ends of the target fragment.

5. The method of claim 1, wherein said immobilization moiety is a biotin moiety.

6. The method of claim 1, wherein said solid phase carries one or more streptavidin moieties.

7. The method of claim 1, wherein said solid phase comprises magnetic beads.

8. The method of claim 1, wherein in step (b) the target fragment-complementary portions of the at least one probe which are complementary to the probe-complementary portions of the target fragment are separated by an intervening non-target fragment-complementary portion, and the method further comprises contacting said fragmented nucleic acid sample with a gap oligonucleotide complementary to said intervening portion.

9. The method of claim 8, wherein said gap oligonucleotide contains one or more amplification primer-binding sequences.

10. The method of claim 8, wherein the said gap oligonucleotide contains one or more barcode sequences, further comprising after step (g) pooling the circularized target fragment with circularized target fragments generated from other samples and subjecting the pooled circularized target fragments to step (h).

11. The method of claim 1, wherein in step (d) the probe-complementary portions of the target fragment are allowed to hybridize with the target-fragment complementary portions of the probe in the presence of formamide.

12. The method of claim 1, further comprising between steps (f) and (g) one or more steps of washing the solid phase, wherein said washing steps are performed in the presence of formamide.

13. The method of claim 1, further comprising between steps (g) and (h) a step of detaching and separating said circularized target fragment from the immobilized probe.

14. The method of claim 1, wherein the circularized target fragment is amplified by PCR, RCA or MDA.

15. The method of claim 8, wherein the circularized target fragment is amplified by PCR or MDA, and said PCR or MDA is primed from primers having binding sites in said gap oligonucleotide and, in the case of MDA, optionally the corresponding portion of the amplification product of the circularized target fragment.

16. The method of claim 15, wherein said PCR primers have 5' tails comprising one or more barcode sequences, further comprising after step (h) pooling the amplified circularized target fragment with amplified circularized target fragments generated from other samples.

17. The method of claim 8, wherein the circularized target fragment is amplified by MDA, wherein said MDA is primed from random primers or from primers having binding sites in said gap oligonucleotide, further comprising a subsequent PCR amplification step wherein said PCR is primed from primers having binding sites in the MDA product sequence corresponding to said gap oligonucleotide and having 5' tails comprising one or more barcode sequences.

18. The method of claim 14, wherein said RCA or MDA is effected using phi29 polymerase.

19. The method of claim 1, wherein said method is for amplifying a plurality of target nucleic acids in a nucleic acid sample and comprises:
(a) subjecting aliquots of said nucleic acid sample to respectively different combinations of one or more restriction endonucleases to create a plurality of target fragments comprising said target nucleic acids, and pooling said aliquots of fragmented nucleic acid sample;
(b) contacting said fragmented nucleic acid sample with a plurality of probes which are provided with an immobilization moiety, wherein said contacting is performed in a hybridization solution containing between 1% and 50% formamide, wherein said probes comprise two target fragment-complementary portions which are complementary in sequence to the probe-complementary portions of the target fragments, and wherein said portions of the probes may be adjacent, or separated by an intervening non-target fragment-complementary portion;
(c) rendering the fragmented nucleic acid sample single-stranded, wherein the step may occur before, contemporaneously with or after step (b);
(d) allowing the probe-complementary portions of the target fragments to hybridize with the target fragment-complementary portions of the probes;
(e) adding a solid phase to immobilize the probe-target fragment hybrids by means of said immobilization moiety;
(f) separating non-immobilized nucleic acid fragments from the solid phase;
(g) washing the solid phase in the presence of formamide;
(h) contacting the solid phase with a ligation solution containing a ligase to ligate, directly or indirectly, ligatable 5' and 3' ends of the target fragments whereby the target fragments are circularized, wherein where one of said probe-complementary portions of the target fragments is not located at an end of the target fragments, the ligatable end, other than that at which a probe-complementary portion is located, is created by the action of a flap endonuclease or an exonuclease;
(i) denaturing the circularized target fragments from the immobilized probes and separating said fragments from the solid phase; and
(j) amplifying said circularized target fragments.

\* \* \* \* \*

UNITED STATES PATENT AND TRADEMARK OFFICE
CERTIFICATE OF CORRECTION

PATENT NO. : 9,657,339 B2  
APPLICATION NO. : 13/512924  
DATED : May 23, 2017  
INVENTOR(S) : Fredrik Roos et al.

Page 1 of 1

It is certified that error appears in the above-identified patent and that said Letters Patent is hereby corrected as shown below:

In the Specification

In Column 1, Line 8, delete "provided" and insert -- provide --, therefor.

In Column 5, Line 38, delete "Ils" and insert -- IIs --, therefor.

In Column 13, Line 39, delete "RecJ$_r$." and insert -- RecJ$_f$. --, therefor.

In Column 17, Line 54, delete "10 µl ." and insert -- 10 µl. --, therefor.

In Column 17, Line 57, delete "HpyCH4111" and insert -- HpyCH4III --, therefor.

In Column 17, Line 59, delete "Eco01091" and insert -- EcoO109I --, therefor.

Signed and Sealed this  
Fifteenth Day of August, 2017

Joseph Matal  
*Performing the Functions and Duties of the*  
*Under Secretary of Commerce for Intellectual Property and*  
*Director of the United States Patent and Trademark Office*